(12) United States Patent
Rahbar et al.

(10) Patent No.: US 6,605,642 B2
(45) Date of Patent: Aug. 12, 2003

(54) INHIBITORS OF FORMATION OF ADVANCED GLYCATION ENDPRODUCTS (AGES)

(75) Inventors: Samuel Rahbar, Encino, CA (US); Iraj Lalezari, Scarsdale, NY (US)

(73) Assignee: City of Hope, Duarte, CA (US)

( * ) Notice: Subject to any disclaimer, the term of this patent is extended or adjusted under 35 U.S.C. 154(b) by 0 days.

(21) Appl. No.: 09/800,976

(22) Filed: Mar. 8, 2001

(65) Prior Publication Data

US 2002/0013256 A1 Jan. 31, 2002

Related U.S. Application Data

(63) Continuation-in-part of application No. 09/543,703, filed on Apr. 5, 2000, now Pat. No. 6,337,350.
(60) Provisional application No. 60/127,835, filed on Apr. 5, 1999.

(51) Int. Cl.$^7$ ............................................. A61K 31/195
(52) U.S. Cl. ...................... 514/563; 514/564; 514/567; 514/330; 562/455; 562/439; 562/457; 546/191
(58) Field of Search ................................ 514/563, 564, 514/567, 330

(56) References Cited

U.S. PATENT DOCUMENTS

| | | | |
|---|---|---|---|
| 4,661,579 A | 4/1987 | Blöcker | 528/170 |
| 4,921,997 A | 5/1990 | Lalezari et al. | 560/34 |
| 5,093,367 A | 3/1992 | Lalezari et al. | 560/34 |
| 5,268,500 A | 12/1993 | Lalezari et al. | 560/34 |
| 5,272,176 A | 12/1993 | Ulrich et al. | 514/399 |
| 5,292,935 A | 3/1994 | Lalezari et al. | 560/34 |
| 5,602,277 A | 2/1997 | Babu et al. | 562/439 |
| 5,661,139 A | 8/1997 | Lankin et al. | 560/34 |
| 5,677,330 A | 10/1997 | Abraham et al. | 514/421 |
| 5,716,987 A | 2/1998 | Wille | 514/557 |
| 5,962,651 A | 10/1999 | Lalezari et al. | 514/6 |

FOREIGN PATENT DOCUMENTS

| | | |
|---|---|---|
| WO | WO 92/07560 | 5/1992 |
| WO | WO 95/31192 | 11/1995 |
| WO | WO 98/55121 | 12/1998 |
| WO | WO 00/59875 A2 | 10/2000 |

OTHER PUBLICATIONS

Samuel Rahbar et al., "Novel Inhibitors of Advanced Glycation Endproducts," Biochemical and Biophysical Research Communications 262(3):651–656, 1999. XP–000946146.

Al–Abed, Y. et al. "Inhibition of advanced glycation endproduct formation by acetaldehyde: Role in the cardioprotective effect of ethanol", *Proc. Natl. Acad. Sci. USA*, Mar. 1999; 96:2385–2390.

Aldrich Catalog 805, 786, 8, and 3, 1994–1995.

Asif, M. et al. An "advanced glycation endproduct cross–link breaker can reverse age–related increases in myocardial stiffness", *Proc. Natl. Acad. Sci.*, Mar. 14, 2000; 97(6):2809–2813.

Beisswenger, P.J. et al., "Metformin Reduces Systemic Methylglyoxal Levels in Type 2 Diabetes", *Diabetes,* Jan. 1999; 48:198–202.

Boel, E. et al. "Diabetic Late Complications: Will Aldose Reductase Inhibitors or Inhibitors of Advanced Glycosylation Endproduct Formation Hold Promise?", *J. Diabetes and Its Complications,* 1995; 9:104–129.

Booth, A.A. et al. "Thiamine Pyrophosphate and Pyridoxamine Inhibit the Formation of Antigenic Advanced Glycation End–Products: Comparison with Aminoguanidine", *Biochem. Biophys. Res. Commun.,* 1996; 220:113–119.

Booth, A.A. et al. "In Vitro Kinetic Studies of Formation of Antigenic Advanced Glycation End Products (AGEs)", *Journal of Biological Chemistry,* Feb. 28. 1997; 272(9):5430–5437.

Calatayud, J.M., "Favorable Effects of the Lipid–Lowering and Platelet Antiaggregant Plafibride on the Aging Process of Mice of the C57BL/6J Strain", Meth and Find Exptl Clin Pharmacol 5(10):707–714, 1983.

Cameron, N.E. et al. "Effects of aminoguanidine on peripheral nerve function and polyol pathway metabolites in streptozotocin–diabetic rats", *Diabetologia;* 1992; 35:946–950.

Cooper, M.E. et al., "The cross–link breaker, N–phenacylthiazolium bromide prevents vascular advanced glycation and end–product accumulation," Diabetologia 43:660–664, 2000.

Corbett, J.A. et al. "Aminoguanidine, a Novel Inhibitor of Nitric Oxide Formation, Prevents Diabetic Vascular Dysfunction", *Diabetes,* Apr. 1992; 42:552–556.

de Gruyter, W., Pschyrembel Klinisches Woerterbuch, 258:47–49, 1998.

(List continued on next page.)

Primary Examiner—Venkataraman Balasubramanian
(74) Attorney, Agent, or Firm—Rothwell, Figg, Ernst & Manbeck

(57) ABSTRACT

The nonenzymatic glycation and crosslinking of proteins is a part of the aging process with the glycation endproducts and crosslinking of long-lived proteins increasing with age. This process is increased at elevated concentrations of reducing sugars in the blood and in the intracellular environment such as occurs with diabetes. The structural and functional integrity of the affected molecules become perturbed by these modifications and can result in severe consequences. The compounds of the present invention can be used to inhibit this process of nonenzymatic glycation and therefore to inhibit some of the ill effects caused by diabetes or by aging. The compounds are also useful for preventing premature aging, spoilage of proteins in food and can prevent discoloration of teeth.

7 Claims, 14 Drawing Sheets

OTHER PUBLICATIONS

Durany, N. et al. "Investigations on oxidative stress and therapeutical implications in dementia", *Eur. Arch. Psychiatry Clin. Neurosci.,* 1999; 249:Suppl. 3 III/68–III/73.

Ferrari, E. et al., "Effects of long–term treatment (4 years) with pentoxifylline on haemorheological changes and vascular complications in diabetic patients," 5(1):26–39, 1987.

Grigoleit, H.G. et al., "Red Blood Cell Aging As a Model to Influence Pharmacologically The Red Cell Filterability," Research in Experimental Medicine 179:249–254, 1981.

Guarnieri, G. et al., "Modulation of Protein Kinetics in Chronic Renal Failure," Miner Electrolyte Metab 23:214–217, 1997.

Hirsch, J., "The reaction of some dicarbonyl sugars with aminoguanidine," Carbohydrate Research 232:125–130, 1992.

Iwafune, Y. et al., "Clinical use of pentoxifylline in haemorrhagic disorders of the retina," Pharmatherapeutica 2:429–438, 1980.

Jakuš, V. et al. "Inhibition of Nonenzymatic Protein Glycation and Lipid Peroxidation by Drugs with Antioxidant Activity", *Life Sciences,* 1999; 65(18–19):1991–1993.

Jyothirmayi, G.N. et al. "Effects of Metformin on Collagen Glycation and Diastolic Dysfunction in Diabetic Myocardium", *J. Cardiovasc. Pharmacol. Therapeut.,* 1998; 3(4):319–326.

Khalifah, R.G. et al., "Amadorins: Novel Post–Amadori Inhibitors of Advanced Glycation Reactions", *Biochem. Biophys. Res. Commun.,* 1999; 257:251–258.

Kochakian, M. et al. "Chronic Dosing with Aminoguanidine and Novel Advanced Glycosylation End Product–Formation Inhibitors Ameliorates Cross–Linking of Tail Tendon Collagen in STZ–Induced Diabetic Rats", *Diabetes,* Dec. 1996; 45:1694–1700.

Lalezari, I. et al. "Synthesis and Investigation of Effects of 2–[4–[[(Arylamino)carbonyl]amino]phenoxy]–2–methyl-propionic Acids on the Affinity of Hemoglobin for Oxygen: Structure–Activity Relationshhips", *J. Med. Chem.,* 1989; 32:2352–2357.

Lalezari, I. et al. "LR–16, a compound with potent effects on the oxygen affinity of hemoglobin, on blood cholesterol, and on low density lipoprotein", *Proc. Natl. Acad. Sci. USA,* Aug. 1988; 85:6117–6121.

Lee, Y. et al., "The Effect of Pentoxifylline on Current Perception Thresholds in Patients With Diabetic Sensory Neuropathy," Journal of Diabetes and Its Complications 11:274–278, 1997.

Malik, N.S. and Meek, K.M. "The Inhibition of Sugar–Induced Structural Alterations in Collagen by Aspirin and Other Compounds", *Biochem. Biophys. Res. Commun.,* 1994; 199(2):683–686.

Marques, C. et al. "Bendazac decreases in vitro glycation of human lens crystallins. Decrease of in vitro protein glycation by bendazac", *Documenta Ophthalmologica,* 1995; 90:395–404.

McCarty, M.F. "Nitric oxide deficiency, leukocyte activation, and resultant ischemia are crucial to the pathogenesis of diabetic retinopathy/neuropathy—preventive potential of antioxidants, essential fatty acids, chromium, ginkgolides, and pentoxifylline," Medical Hypothesis 50:435–449, May 1998.

Menzel, E.J. et al. "Comparison of the effect of different inhibitors on the non–enzymatic glycation of rat tail tendons and bovine serum albumin", *Ann. Clin. Biochem.,* 1996; 3:241–248.

Miwa, I. et al., "Inhibition of Advanced Protein Glycation by 8–Quinolinecarboxylic Hydrazide", *Pharmacology,* 1996; 52:314–320.

Morimitsu, Y. et al. "Protein Glycation Inhibitors from Thyme (*Thymus vulgaris*)", *Biosci. Biotech. Biochem.,* 1995; 59(11):2018–2021.

Münch, G. eta l. "Influence of advanced glycation end–products and AGE–inhibitors on nucleation–dependent polymerization of β–Amyloid peptide", *Biochimica et Biophysica Acta,* 1997; 1360:17–29.

Münch, G. et al. "Advanced glycation endproducts in ageing and Alzheimer's disease", *Brain Research Reviews,* 1997; 23:134–143.

Nakamura, S. et al. "Progression of Nephropathy in Spontaneous Diabetic Rats is Prevented by OPB–9195, a Novel Inhibitor of Advanced Glycation", *Diabetes,* May 1997; 46:895–899.

Navarro, J.F. et al. "Pentoxifylline (PTF) reduces proteinuria and tumor necrosis factor–alpha TNFa) in diabetic patients with advanced renal failure," J. of the American Society of Nephrology 9:120A, Sep. 1998.

Parnetti, L. et al., "The role of haemaorheological factors in the ageing Brain: long–term therapy with pentoxifylline ('Trental' 400) in elderly patients with initial mental deterioration," Pharmatherapeutica 4:617–627, 1986.

Qiang, X. et al., "Inhibitory effect of troglitazone on diabetic neuropathy in streptozotocin–induced diabetic rats," Diabetologia 41:1321–1326, Nov. 1998.

Rahbar, S. and Nadler, J.L. "A new rapid method to detect inhibition of Amadori product generated by δ–gluconolactone", *Clinica Chimica Acta,* 1999; 287:123–130.

Rahbar, S. et al. "Novel Inhibitors of Advanced Glycation Endproducts", *Biochem. Biophys. Res. Commun.,* 1999; 262:651–656.

Raj, D.S.C., "Advanced Glycation End Products: A Nephrologist's Perspective," American Journal of Kidney Diseases 35(3):365–380, Mar. 2000.

Ruggiero–Lopez, D. et al. "Reaction of Metformin with Dicarbonyl Compounds. Possible Implication in the Inhibition of Advanced Glycation End Product Formation", *Biochem. Pharmacology,* 1999; 58:1765–1773.

Ryan, M.E. et al. "Tetracyclines Inhibit Protein Glycation in Experimental Diabetes", *Adv. Dent. Res.,* Nov. 1998; 12:152–158.

Sensi, M. et al. "D–Lysine reduces the non–enzymatic glycation of proteins in experimental diabetes mellitus in rats", *Diabetologia,* 1993; 36:797–801.

Solerte, S.B. et al., "Pentoxifylline, Total Urinary Protein Excretion Rate and Arterial Blood Pressure in Long–Term Insulin–Dependent Diabetic Patients with Overt Nephropathy," Acta Diabetologia Latina 24:229–239, 1987.

Sonkin, P.L. et al., "Pentoxifylline Modulates Deformability, F–actin Content, and Superoxide Anion Production of Polymorphonuclear Leukocytes from Diabetic Cats," Experimental Eye Research 55:831–838, 1992.

Soulis, T. et al. "Relative contributions of advanced glycation and nitric oxide synthase inhibition to aminoguanidine––mediated renoprotection in diabetic rats", *Diabetologia,* 1997; 40:1141–1151.

Soulis, T. et al. "A novel inhibitor of advanced glycation end–product formation inhibits mesenteric vascular hypertrophy in experimental diabetes", *Diabetologia* 1999; 42:472–479.

Swamy–Mruthinti, S. et al. "Acetyl–L–Carnitine Decreases Glycation of Lens Proteins: in vitro Studies", *Exp. Eye Res.,* 1999; 69:109–115.

Taguchi, T. et al. "Inhibition of advanced protein glycation by a Schiff base between aminoguanidine and pyridoxal", *European Journal of Pharmacology,* 1999; 378:283–289.

Tanaka, Y. et al. "Effect of metformin on advanced glycation endproduct formation and peripheral nerve function in streptozotocin–induced diabetic rats", *European Journal of Pharmacology,* 1999; 376:17–22.

The Merck Index, paragraphs 462, 1927 and 4857, 1996.

Thornalley, P.J. et al., "Rapid Hydrolysis and Slow $\alpha,\beta$–Dicarbonyl Cleavage of an Agent Proposed to Cleave Glucose–Derived Protein Cross–Links," Biochemical Pharmacology 57:303–307, 1999.

Tilton, R.G. et al. "Prevention of Diabetic Vascular Dysfunction by Guanidines. Inhibition of Nitric Oxide Synthase Versus Advanced Glycatin End–Product Formation", *Diabetes,* Feb. 1993; 42:221–232.

Tsuchida, K. et al., "Suppression of transforming growth factor beta and vascular endothelial growth factor in diabetic nephropathy in rats by a novel advanced glycation end product inhibitor, OPB–9195", *Diabetologia,* 1999; 42:579–588.

Ulrich, P. and Zhang, X. "Pharmacological reversal of advanced glycation end–product mediated protein crosslinking", *Diabetologia,* 1997; 40:S157–S159.

van Boekel, M.A.M. et al. "Glycation of human serum albumin: inhibition of Diclofenac", *Biochimica et Biophysica Acta,* 1992; 1120:201–204.

Vasan, S. et al. "An agent cleaving glucose–derived protein crosslinks in vitro and in vivo", *Nature,* Jul. 18, 1996; 382:275–278.

Wolffenbuttel, B.H.R. et al. "Breakers of advanced glycation end products restore large artery properties in experimental diabetes", *Proc. Natl. Acad. Sci. USA,* Apr. 1998; 95:4630–4634.

INHIBITORS OF FORMATION OF ADVANCED GLYCATION ENDPRODUCTS (AGES)

CROSS REFERENCE TO RELATED APPLICATIONS

This application is a continuation-in-part of application Ser. No. 09/543,703, filed Apr. 5, 2000, now U.S. Pat. No. 6,337,350, which is related to provisional application Ser. No. 60/127,835, filed Apr. 5, 1999, which are incorporated herein by reference.

BACKGROUND OF THE INVENTION

The present invention relates generally to the modification and aging of proteins through reaction with glucose and other reducing sugars, such as fructose or ribose and more particularly to the inhibition of nonenzymatic glycation of proteins which often results in formation of advanced glycation endproducts and crosslinks.

An elevated concentration of reducing sugars in the blood and in the intracellular environment results in the nonenzymatic formation of glycation and dehydration condensation complexes known as advanced glycation end-products (AGEs). These complex products form on free amino groups on proteins, on lipids and on DNA (Bucala and Cerami, 1992; Bucala et al., 1993; Bucala et al., 1984). This phenomenon is called "browning" or "Maillard" reaction and was discovered early in this century by the food industry (Maillard, 1916). The significance of a similar process in biology became evident only after the discovery of the glycosylated hemoglobins and their increased presence in diabetic patients (Rahbar, 1968; Rahbar et al., 1969). In human diabetic patients and in animal models of diabetes, these nonenzymatic reactions are accelerated and cause increased AGE formation and increased glycation of long-lived proteins such as collagen, fibronectin, tubulin, lens crystallin, myelin, laminin and actin, in addition to hemoglobin and albumin, and also of LDL associated lipids and apoprotein. Moreover, brown pigments with spectral and fluorescent properties similar to those of late-stage Maillard products have also been found in vivo in association with several long-lived proteins such as lens crystallin proteins and collagen from aged individuals. An age-related linear increase in pigments was observed in human dura collagen between the ages of 20 to 90 years. AGE modified proteins increase slowly with aging and are thought to contribute to normal tissue remodeling. Their level increases markedly in diabetic patients as a result of sustained high blood sugar levels and lead to tissue damage through a variety of mechanisms including alteration of tissue protein structure and function, stimulation of cellular responses through AGE specific receptors or the generation of reactive oxygen species (ROS) (for a recent review see Boel et al., 1995). The structural and functional integrity of the affected molecules, which often have major roles in cellular functions, become perturbed by these modifications, with severe consequences on affected organs such as kidney, eye, nerve, and micro-vascular functions (Silbiger et al., 1993; Brownlee et al., 1985).

Structural changes on macromolecules by AGEs are known to accumulate under normal circumstances with increasing age. This accumulation is severely accelerated by diabetes and is strongly associated with hyperglycemia. For example, formation of AGE on protein in the subendothelial basement membrane causes extensive cross-link formation which leads to severe structural and functional changes in protein/protein and protein/cell interaction in the vascular wall (Haitoglou et al., 1992; Airaksinen et al., 1993).

Enhanced formation and accumulation of advanced glycation end products (AGEs) have been implicated as a major pathogenesis process leading to diabetic complications, normal aging, atherosclerosis and Alzheimer's disease. This process is accelerated by diabetes and has been postulated to contribute to the development of a range of diabetic complications including nephropathy (Nicholls and Mandel, 1989), retinopathy (Hammes et al., 1991) and neuropathy (Cameron et al., 1992). Particularly, tissue damage to the kidney by AGEs leads to progressive decline in renal function and end-stage renal disease (ESRD) (Makita et al., 1994), and accumulation of low-molecular-weight (LMW) AGE peptides (glycotoxins) (Koschinsky et al., 1997) in the serum of patients with ESRD (Makita et al., 1991). These low molecular weight (LMW)-AGEs can readily form new crosslinks with plasma or tissue components, e.g., low density lipoprotein (LDL) (Bucala et al., 1994) or collagen (Miyata et al., 1993) and accelerate the progression of tissue damage and morbidity in diabetics.

Direct evidence indicating the contribution of AGEs in the progression of diabetic complications in different lesions of the kidneys, the rat lens and in atherosclerosis has recently been reported (Vlassara et al., 1994; Vlassara et al., 1995; Horie et al., 1997; Matsumoto et al., 1997; Soulis-Liparota et al., 1991; Bucala and Vlassara, 1997; Bucala and Rahbar, 1998; Park et al., 1998). Indeed, the infusion of pre-formed AGEs into healthy rats induces glomerular hypertrophy and mesangial sclerosis, gene expression of matrix proteins and production of growth factors (Brownlee et al., 1991; Vlassara et al., 1995). Several lines of evidence indicate that the increase in reactive carbonyl intermediates (methylglyoxal, glycolaldehyde, glyoxal, 3-deoxyglucosone, malondialdehyde and hydroxynonenal) is the consequence of hyperglycemia in diabetes. "Carbonyl stress" leads to increased modification of proteins and lipids, followed by oxidant stress and tissue damage (Baynes and Thorpe, 1999; Onorato et al., 1998; McLellan et al., 1994). Further studies have revealed that aminoguanidine (AG), an inhibitor of AGE formation, ameliorates tissue impairment of glomeruli and reduces albuminuria in induced diabetic rats (Soulis-Liparota et al., 1991; Itakura et al., 1991). In humans, decreased levels of hemoglobin (Hb)-AGE (Makita et al., 1992) concomitant with amelioration of kidney function as the result of aminoguanidine therapy in diabetic patients, provided more evidence for the importance of AGEs in the pathogenesis of diabetic complications (Bucala and Vlassara, 1997).

The global prevalence of diabetes mellitus, in particular in the United States, afflicting millions of individuals with significant increases of morbidity and mortality, together with the great financial burden for the treatment of diabetic complications in this country, are major incentives to search for and develop drugs with a potential of preventing or treating complications of the disease. So far the mechanisms of hyperglycemia-induced tissue damage in diabetes are not well understood. However, four pathogenic mechanisms have been proposed, including increased polyol pathway activity, activation of specific protein kinase C (PKC) isoforms, formation and accumulation of advanced glycation endproducts, and increased generation of reactive oxygen species (ROS) (Kennedy and Lyons, 1997). Most recent immunohistochemical studies on different tissues from kidneys obtained from ESRD patients (Horie et al., 1997) and diabetic rat lenses (Matsumoto et al., 1997), by using specific antibodies against carboxymethyllysine (CML), pentosidine, the two known glycoxidation products and pyrraline, have localized these AGE components in different lesions of the kidneys and the rat lens, and have provided more evidence in favor of protein-AGE formation in close association with generation of ROS to be major factors in causing permanent and irreversible modification of tissue proteins. Therefore, inhibitors of AGE formation and antioxidants hold promise as effective means of prevention and treatment of diabetic complications.

The Diabetic Control and Complications Trial (DCCT), has identified hyperglycemia as the main risk factor for the development of diabetic complications (The Diabetes Control and Complications Trial Research Group, 1993). Compelling evidence identifies the formation of advanced glycation endproducts as the major pathogenic link between hyperglycemia and the long-term complications of diabetes (Makita et al., 1994; Koschinsky et al., 1997; Makita et al., 1993; Bucala et al., 1994; Bailey et al., 1998).

The reactions between reducing sugars and amino groups of proteins, lipids and DNA undergo a series of reactions through dicarbonyl intermediates to generate advanced glycation endproducts (Bucala and Cerami, 1992; Bucala et al., 1993; Bucala et al., 1984).

In human diabetic patients and in animal models of diabetes, AGE formation and accumulation of long-lived structural proteins and lipoproteins have been reported. Most recent reports indicate that glycation inactivates metabolic enzymes (Yan and Harding, 1999; Kato et al., 2000; Verbeke et al., 2000; O'Harte et al., 2000). The structural and functional integrity of the affected molecules which often have major roles in cellular functions become perturbed by these modifications, with severe consequences on affected organs such as kidney, eye and nerve and on microvascular functions (Boel et al., 1995; Silbiger et al., 1993). The glycation-induced change of immunoglobin G is of particular interest. Recent reports of glycation of the Fab fragment of IgG in diabetic patients suggest that immune deficiency observed in these patients may be explained by this phenomenon (Lapolla et al., 2000). Furthermore, an association between IgM response to IgG damaged by glycation and disease activity in rheumatoid arthritis have been reported recently (Lucey et al., 2000). Also, impairment of high-density lipoprotein function by glycation has been described (Hedrick et al., 2000).

Methylglyoxal (MG) has recently received considerable attention as a common mediator and the most reactive dicarbonyl to form AGEs (Phillips and Thornalley, 1993; Beisswenger et al., 1998). It is also a source of reactive oxygen species (ROS) (free radicals) generation in the course of glycation reactions (Yim et al., 1995).

Nature has devised several humoral and cellular defense mechanisms to protect tissues from the deleterious effects of "carbonyl stress" and accumulation of AGEs, e.g., the glyoxylase systems (I and II) and aldose reductase catalyze the detoxification of MG to D-lactate (McLellan et al., 1994). Amadoriases are also a novel class of enzymes found in Aspergillus which catalyze the deglycation of Amadori products (Takahashi et al., 1997). Furthermore, several AGE-receptors have been characterized on the surface membranes of monocytes and on macrophage, endothelial, mesangial and hepatic cells. One of these receptors, RAGE, a member of the immunoglobulin superfamily, has been found to have a wide tissue distribution (Schmidt et al., 1994; Yan et al., 1997). The discovery of various natural defense mechanisms against glycation and AGE formation suggests an important role of AGEs in the pathogenesis of vascular and peripheral nerve damage in diabetes. MG binds to and irreversibly modifies arginine and lysine residues in proteins. MG modified proteins have been shown to be ligands for the AGE receptor (Westwood et al., 1997) indicating that MG modified proteins are analogous (Schalkwijk et al., 1998) to those found in AGEs. Furthermore, glycolaldehyde, a reactive intermediate in AGE formation, generates an active ligand for macrophage scavenger receptor (Nagai et al., 2000). The effects of MG on LDL have been characterized in vivo and in vitro (Bucala et al., 1993).

Lipid peroxidation of polyunsaturated fatty acids (PUFA), such as arachidonate, also yield carbonyl compounds; some are identical to those formed from carbohydrates (Al-Abed et al., 1996), such as MG and GO, and others are characteristic of lipid, such as malondialdehyde (MDA) and 4-hydroxynonenal (HNE) (Requena et al., 1997). The latter two carbonyl compounds produce lipoxidation products (Al-Abed et al., 1996; Requena et al., 1997). A recent report emphasizes the importance of lipid-derived MDA in the cross-linking of modified collagen and in diabetes mellitus (Slatter et al., 2000). A number of AGE compounds, both fluorophores and nonfluorescent, are involved in crosslinking proteins and have been characterized (Baynes and Thorpe, 1999). In addition to glucose derived AGE-protein crosslinks, AGE crosslinking also occurs between tissue proteins and AGE-containing peptide fragments formed from AGE-protein digestion and turnover. These reactive AGE-peptides, now called glycotoxins, are normally cleared by the kidneys. In diabetic patients, these glycotoxins react with the serum proteins and are a source for widespread tissue damage (He et al.,1999). However, detailed information on the chemical nature of the crosslink structures remain unknown. The crosslinking structures characterized to date, on the basis of chemical and spectroscopic analyses, constitute only a small fraction of the AGE crosslinks which occur in vivo, with the major crosslinking structure(s) still unknown. Most recently, a novel acid-labile AGE-structure, N-omega-carboxymethylarginine (CMA), has been identified by enzymatic hydrolysis of collagen. Its concentration was found to be 100 times greater than the concentration of pentosidine (Iijima et al., 2000) and it is assumed to be a major AGE crosslinking structure.

In addition to aging and diabetes, the formation of AGEs has been linked with several other pathological conditions. IgM anti-IgG-AGE appears to be associated with clinical measurements of rheumatoid arthritis activity (Lucey et al., 2000). A correlation between AGEs and rheumatoid arthritis was also made in North American Indians (Newkirk et al., 1998). AGEs are present in brain plaques in Alzheimer's disease and the presence of AGEs may help promote the development of Alzheimer's disease (Durany et al., 1999; Munch et al., 1998; Munch et al., 1997). Uremic patients have elevated levels of serum AGEs compared to age-matched controls (Odani et al., 1999; Dawnay and Millar, 1998). AGEs have also been correlated with neurotoxicity (Kikuchi et al., 1999). AGE proteins have been associated with atherosclerosis in mice (Sano et al., 1999) and with atherosclerosis in persons undergoing hemodialysis (Takayama et al., 1998). A study in which aminoguanidine was fed to rabbits showed that increasing amounts of aminoguanidine led to reduced plaque formation in the aorta thus suggesting that advanced glycation may participate in atherogenesis and raising the possibility that inhibitors of advanced glycation may retard the process (Panagiotopoulos et al., 1998). Significant deposition of N(epsilon)-carboxymethyl lysine (CML), an advanced glycation endproduct, is seen in astrocytic hyaline inclusions in persons with familial amyotrophic lateral sclerosis but is not seen in normal control samples (Kato et al., 1999; Shibata et al., 1999). Cigarette smoking has also been linked to increased accumulation of AGEs on plasma low density lipoprotein, structural proteins in the vascular wall, and the lens proteins of the eye, with some of these effects possibly leading to pathogenesis of atherosclerosis and other diseases associated with tobacco usage (Nicholl and Bucala, 1998). Finally, a study in which aminoguanidine was fed to rats showed that the treatment protected against progressive cardiovascular and renal decline (Li et al., 1996).

The mechanism of the inhibitory effects of aminoguanidine in the cascade of glycosylation events has been investigated. To date, the exact mechanism of AG-mediated inhibition of AGE formation is not completely known. Several lines of in vitro experiments resulted in contrasting conclusions. Briefly, elevated concentrations of reducing sugars cause spontaneous reactions between carbohydrate carbonyl and protein amino groups leading to:

1. Reversible formation of Schiff's bases followed by
2. Amadori condensation/dehydration products such as 3-deoxyglucason (3-DG), a highly reactive dicarbonyl compound (Kato et al., 1990).
3. Irreversible and highly reactive advanced glycosylation endproducts. Examples of early Amadori products are ketoamines which undergo further condensation reactions to form late AGEs. A number of AGE products have been purified and characterized recently, each one constituting only minor fractions of the in vivo generated AGEs. Examples are pyrraline, pentosidine, carboxymethyl-lysine (CML), carboxyethyl-lysine (CEL), crossline, pyrrolopyridinium, methylglyoxal lysine dimer (MOLD), Arg-Lys imidazole, arginine pyridinium, cypentodine, piperidinedinone enol and alkyl, formyl, diglycosyl-pyrrole (Vlassara, 1994).

Analysis of glycation products formed in vitro on a synthetic peptide has demonstrated that aminoguanidine does not inhibit formation of early Amadori products (Edelstein and Brownlee, 1992). Similar conclusions were reached by analysis of glycation products formed on BSA (Requena et al., 1993). In both experiments AGE formation was strongly inhibited by AG as analyzed by fluorescence measurements and by mass spectral analysis. The mass spectral analysis did not detect peptide complexes with molecular mass corresponding to an incorporation of AG in the complex. Detailed mechanistic studies using NMR, mass spectroscopy and X-ray diffraction have shown that aminoguanidine reacts with AGE precursor 3-DG to form 3-amino-5- and 3-amino-6-substituted triazines (Hirsch et al., 1992). In contrast, other experiments using labeled $^{14}$C-AG with lens proteins suggest that AG becomes bound to the proteins and also reacts with the active aldose form of free sugars (Harding, 1990).

Several other potential drug candidates as AGE inhibitors have been reported recently. These studies evaluated the agent's ability to inhibit AGE formation and AGE-protein crosslinking compared to that of aminoguanidine (AG) through in vitro and in vivo evaluations (Nakamura et al., 1997; Kochakian et al., 1996). A recent breakthrough in this field is the discovery of a compound, N-phenacylthiazolium bromide (PTB), which selectively cleaves AGE-derived protein crosslinks in vitro and in vivo (Vasan et al., 1996; Ulrich and Zhang, 1997). The pharmacological ability to break irreversible AGE-mediated protein crosslinking offers potential therapeutic use.

It is well documented that early pharmaceutical intervention against the long-term consequences of hyperglycemia-induced crosslinking, prevent the development of severe late complications of diabetes. The development of nontoxic and highly effective drugs that completely stop glucose-mediated crosslinking in the tissues and body fluids is a highly desirable goal. The prototype of the pharmaceutical compounds investigated both in vitro and in vivo to intervene with the formation of AGEs on proteins is aminoguanidine (AG), a small hydrazine-like compound (Brownlee et al., 1986). However, a number of other compounds were found to have such an inhibitory effect on AGE formation. Examples are D-lysine (Sensi et al., 1993), desferrioxamine (Takagi et al., 1995), D-penicillamine (McPherson et al., 1988), thiamine pyrophosphate and pyridoxamine (Booth et al., 1997) which have no structural similarities to aminoguanidine.

Clinical trials of AG as the first drug candidate intended to inhibit AGE formation are in progress (Corbett et al., 1992). A number of hydrazine-like and non-hydrazine compounds have been investigated. So far AG has been found to be the most useful with fewer side effects than other tested compounds of the prior art. However, AG is a well known selective inhibitor of nitric oxide (NO) and can also have antioxidant effects (Tilton et al., 1993).

A number of other potential drug candidates to be used as AGE inhibitors have been discovered recently and evaluated both in vitro and in vivo (Nakamura et al., 1997; Soulis et al., 1997). While the success in studies with aminoguanidine and similar compounds is promising, the need to develop additional inhibitors of AGEs continues to exist in order to broaden the availability and the scope of this activity and therapeutic utility.

SUMMARY OF THE INVENTION

Derivatives of phenoxyisobutyric acids and of benzoic acid, including aryl and heterocyclic ureido derivatives and aryl and heterocyclic carboxamido derivatives, have been found to inhibit the nonenzymatic glycation of proteins which often results in formation of advanced glycation endproducts and crosslinks. Many other phenoxyisobutyric acid derivatives as well as certain other compounds as set out below also have been found to inhibit the nonenzymatic glycation of proteins. The nonenzymatic glycation and crosslinking of proteins is a part of the aging process with the glycation endproducts and crosslinking of long-lived proteins increasing with age. This process is increased at elevated concentrations of reducing sugars in the blood and in the intracellular environment such as occurs with diabetes. The structural and functional integrity of the affected molecules become perturbed by these modifications and can result in severe consequences. The compounds of the present invention can be used to inhibit this process of nonenzymatic glycation and crosslinking and therefore to inhibit some of the ill effects caused by diabetes or by aging. The compounds are also useful for preventing premature aging, rheumatoid arthritis, Alzheimer's disease, uremia, neurotoxicity, atherosclerosis, and spoilage of proteins in food and can prevent discoloration of teeth.

BRIEF DESCRIPTION OF THE FIGURES

FIG. 4A shows the inhibition of crosslinking of collagen-AGE-BSA by LR23, LR99 and LR102, each at 0.2 mM. FIG. 4B shows the inhibition of crosslinking of collagen-AGE-BSA by LR96 at concentrations of 0.1, 0.2 and 0.5 mM. FIG. 4C shows the inhibition of crosslinking of collagen-AGE-BSA by LR102 at concentrations of 0.1, 0.2 and 0.5 mM.

DETAILED DESCRIPTION OF THE INVENTION

Figure 16:
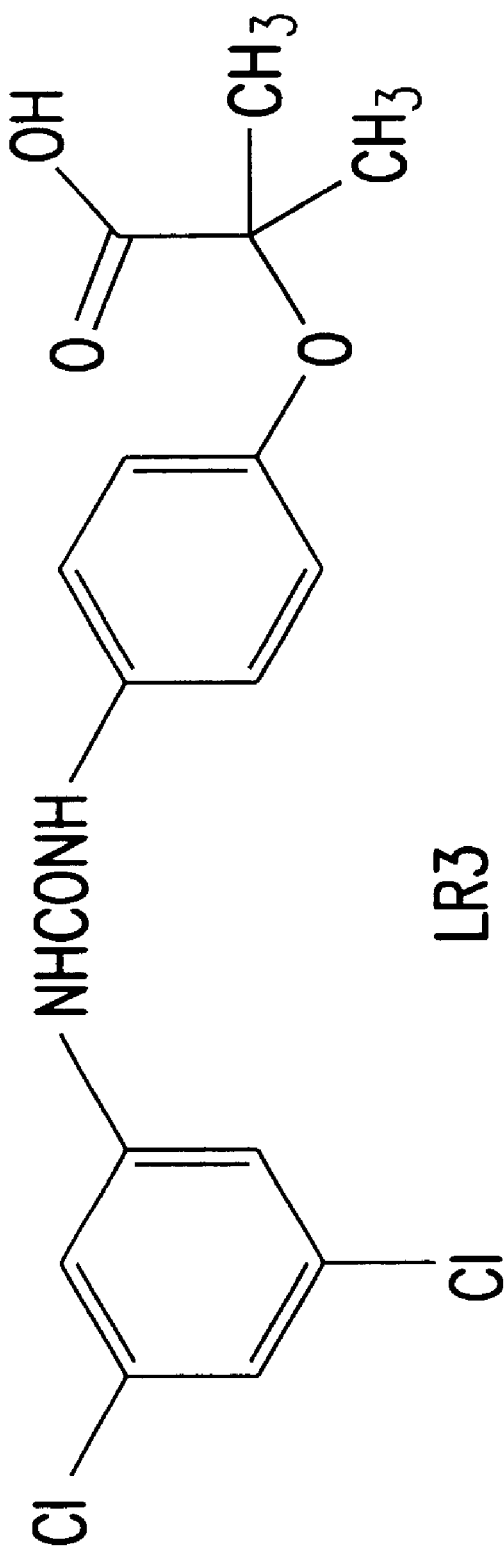
FIG. 16 shows the structure of compound LR3.

We have previously reported new classes of compounds which are aryl (and heterocyclic) ureido and aryl (and heterocyclic) carboxamido phenoxyisobutyric acids and also benzoic acid derivatives and related compounds as inhibitors of glycation and AGE formation (Rahbar et al., 1999; Rahbar et al., 2000). In the course of screening different classes of organic compounds for investigation of their possible inhibitory effects on advanced glycation endproducts (AGEs), we found that most of the phenylureido substituted phenoxy propionic acid derivatives tested have inhibitory effects and several of these compounds were potent inhibitors of AGE-formation at concentrations much lower than an equally inhibiting concentration of aminoguanidine. The aim of the present study was to develop classes of novel inhibitors of glycation, AGE formation and AGE-crosslinking and to investigate their effects through in vitro chemical and immunochemical assays. A total of 102 compounds were designed and synthesized. The first 92 compounds have been reported elsewhere. The ten novel compounds reported here were designed and developed based upon the previously reported LR23 (4-(3,5-dichlorophenylureido)-phenoxyisobutyryl-1-amidocyclohexane-1-carboxylic acid)) which was one of the most powerful inhibitors reported previously (Rahbar et al., 1999; U.S. patent application Ser. No. 09/543,703 which is incorporated herein by reference). These compounds are based upon LR3 (see FIG. 16), the synthesis of which is reported in Lalezari and Lalezari (1989) which is incorporated herein. Considerable increase in the inhibitory potencies, particularly on inhibition of AGE-protein-crosslinking, were found in the three compounds LR96, LR99 and LR102 (see below) as compared to the prototype LR23 and are 2 to 3 times more effective than pyridoxamine (Khalifah etal., 1999).

The mechanism(s) by which this class of compounds inhibits glycation, AGE-formation, and crosslinking is yet to be known. The present study indicates that these compounds are powerful inhibitors that act at multiple steps of glycation and AGE-formation, i.e., early stage, as evidenced by lowering HbAlc levels in the δ-Glu assay, a specific assay for the early stage of glycation (type A or B inhibitor). Most of these compounds strongly inhibit the post-Amadori glycation as demonstrated by the BSA-glucose and G.K.-Ribose assays (type D inhibitors), and a good number of them are powerful inhibitors of AGE protein crosslinking, as evidenced by a specific ELISA assay (type E inhibitors as described by Baynes Classification (Khalifah et al., 1999)).

The mechanism of the inhibitory activities of guanidino compound inhibitors such as two known inhibitors of glycation (aminoguanidine and metformin) is that they are postulated to trap MG and other α-dicarbonyl intermediates of glycation. A most recent study has documented the reaction of metformin with MG and glyoxal (GO), forming guanidino-dicarbonyl adducts further supporting this idea (Ruggiero-Lopez et al., 1999). However, the structures of our novel compounds suggest that they are unlikely to trap α-dicarbonyls. They may be working by a different mechanism distinct from that of aminoguanidine.

Using new assay methods specific for the early (Amadori) and late (post-Amadori) stages of glycation revealed some inhibitors to have greater effects in the early stage and some in the late stage of glycation. However, most of the inhibitor compounds we have investigated are multistage inhibitors. The reaction of reducing sugars with α- and ε-amino groups of proteins is not a random process but rather a site specific reaction which depends on the nature and the vicinity of these chemical groups. The future task is to specifically define the site(s) of interaction of an inhibitor compound in the complex series of reactions and intermediate substrates, leading to AGE formation and cross-linking.

The development of the novel inhibitors of glycation, AGE formation, and AGE-protein crosslinking not only expands the existing arsenals of inhibitors of glycation reaction that can find therapeutic applications for the prevention of diabetic complications, as well as the prevention of other diseases associated with increased glycation of proteins or lipids. Furthermore, the availability of these compounds may prove useful as tools to study the cascade of reactions and intermediate substrate in the process of AGE-formation and AGE-protein cross-linking.

The compounds and their useful compositions utilized in the present invention contain agents capable of reacting with the highly active carbonyl intermediate of an early glycation product thereby preventing those early products from later forming the advanced glycation endproducts which lead to protein crosslinking and to protein aging.

Other utilities envisioned for the present invention are: prevention of premature aging and of spoilage of the proteins in foodstuffs (U.S. Pat. No. 5,661,139). The present agents are also useful in the area of oral hygiene as they prevent discoloration of teeth.

Compounds

Compounds of the present invention are shown in FIGS. 6–15 as LR93–LR102, and were screened for inhibitory effects on protein glycation and AGE-formation.

The above compounds are capable of inhibiting the formation of advanced glycation end products on target proteins and the resulting protein crosslinking. The rationale of the present invention is to use agents which block the post-glycation step, i.e., the formation of fluorescent chromophores, the presence of which chromophore is associated with and leads to adverse sequelae of diabetes and aging. An ideal agent would prevent the formation of the chromophore and its associated crosslinks of proteins and trapping of proteins on the other proteins, such as occurs in arteries and in the kidneys. The compounds of the invention may be administered to mammals including humans to prevent or reduce protein glycation and crosslinking (protein aging). The compounds may be administered orally at variable dosage depending on the activity of each agent in a single or individual amounts. In addition the compounds may be administered parenterally or rectally. The compounds of the invention, the rationale behind the different assay methods of the present invention, and their use are illustrated by the following Examples.

EXAMPLE 1

Hemoglobin-δ-Gluconolactone (δ-Glu) Assay

The δ-Glu assay is a specific method for investigation of inhibitors of the early stage of glycation. Evaluation of early glycation products (Amadori) formation on hemoglobin (HbA$_{1C}$) is performed by incubating red blood cells with an oxidized form of glucose in the presence and the absence of the inhibitor compound followed by determination of HbA$_{1C}$ in the test versus the control (Rahbar and Nadler., 1999). This test is based on a recent report by Lindsay et al. (1997). δ-Glu, an oxidized analogue of glucose, can react rapidly with hemoglobin within the red cells and significantly increases the HbA$_{1C}$ levels within hours after incubation. By contrast, glucose requires weeks for an equivalent reaction to occur. We have used this finding to devise an assay method to measure early stage glycation of hemoglobin (Amadori product) and an assay to evaluate the ability of an inhibitor to inhibit HbA$_{1C}$ formation. Briefly, fresh blood was drawn in potassium-EDTA and prepared for incubation within 30 minutes of collection by mixing 200 μL of blood with 40 μL of either phosphate buffered-saline (PBS), pH 7.4, alone, PBS containing 50 millimoles/L δ-Glu (Sigma), or PBS containing 50 millimoles/L δ-Glu plus 1 millimole/L inhibitor. After incubation for 16 hours at 37° C., the percentage of glycated hemoglobin present was determined. The percentage of glycated Hb (HbA$_{1C}$) was determined using a dedicated ion-exchange HPLC system (BIORAD DIAMAT). Blood samples were analyzed in triplicate. The % inhibition of HbA$_{1C}$ formation by the compound was calculated according to the following formula:

$$((B-C)/(B-A)) \times 100$$

where A is HbA$_{1C}$ concentration in the baseline control tube not treated with δ-Glu, B is the HbA$_{1C}$ concentration in blood incubated with δ-Glu, C is the HbA$_{1C}$ content of the test tube treated both with δ-Glu and the inhibitor compound.

Figure 1:
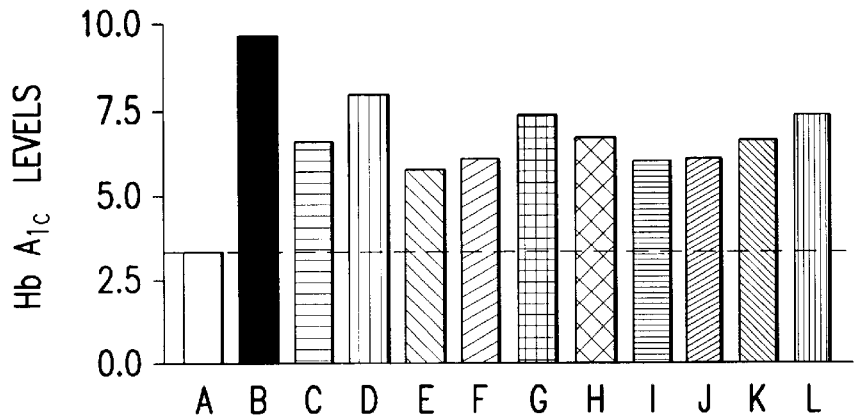
FIG. 1 shows the inhibition by LR93–LR102 in the δ-Glu assay. A—baseline control; B—δ-Glu treated blood; C-L are δ-Glu treated blood plus inhibitor, the inhibitors being as follow: C—LR93; D—LR94; E—LR95; F—LR96; G—LR97; H—LR98; I—LR99; J—LR100; K—LR101; and L—LR102.

The amount of (HbA$_{1C}$) formation using δ-Glu treated whole blood from normal volunteers using 1 millimole/L of the compounds is shown in FIG. 1. The results, calculated as percent inhibition of HbA$_{1c}$ formation, are shown in Table 1. Levels of HbA$_{1C}$ in the δ-Glu treated blood is twice as high as the baseline control. Various inhibitors (compounds LR93–LR102) show different levels of HbA$_{1C}$ depending on their inhibitory potencies. Half of the new compounds exhibited better inhibition than the prototype LR23.

TABLE 1

Percent Inhibition by LR93–LR102 in the δ-Glu Assay

| Compound | Percent Inhibition |
| --- | --- |
| AG | 12.1 |
| LR93 | 49.2 |
| LR94 | 28.5 |
| LR95 | 61.9 |
| LR96 | 57.1 |
| LR97 | 36.5 |
| LR98 | 42.8 |
| LR99 | 53.9 |
| LR100 | 52.4 |
| LR101 | 44.4 |
| LR102 | 31.7 |

The above experiment suggests that this type of drug therapy has benefits in reducing the pathology associated with the formation of early glycation products, a preliminary step in the advanced glycation end product formation.

EXAMPLE 2

BSA-Glucose Assay

This test is used to evaluate the ability of the inhibitors to inhibit glucose-mediated development of fluorescence of BSA (Ikeda et al., 1996). Triplicate samples of BSA (fraction V, essentially fatty acid free, low endotoxin) from Sigma 50 mg/mL and 800 mM glucose (144 mg/mL) in 1.5 M phosphate buffer pH 7.4 containing NaN$_3$ 0.2 g/L was incubated under aseptic conditions at 37° C. for 7 days in the presence or absence of various concentrations of the compounds. After 7 days of incubation each sample was examined for the development of specific fluorescence (excitation, 330 nm; emission, 410 nm). The % inhibition of AGE formation in the test sample versus control was calculated for each inhibitor compound. Aminoguanidine (50 mM) was used as a positive control. The results are shown in Table 2.

Figure 2:
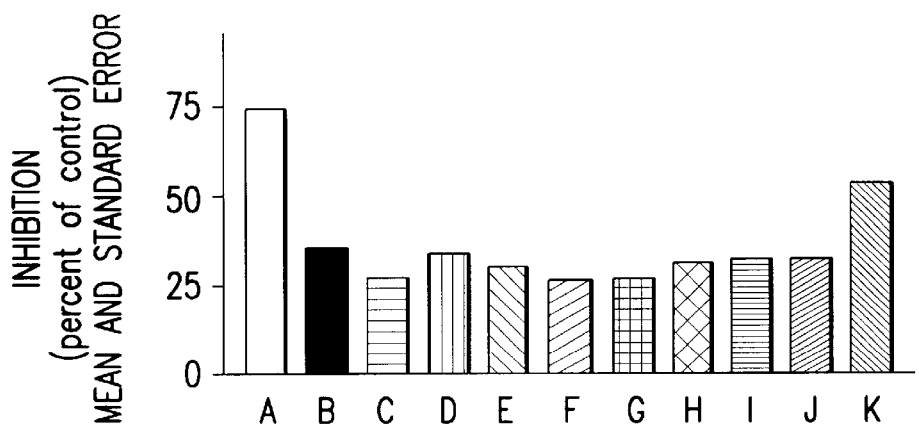
FIG. 2 shows the inhibition by LR93–LR102 in the BSA-Glucose Assay. A—AG (50 mM); B—LR93; C—LR94; D—LR95; E—LR96; F—LR97; G—LR98; H—LR99; I—LR100; J—LR101; and K—LR102.

FIG. 2 shows the inhibitory effects of 1 millimole/L of the new inhibitor versus 50 millimoles/L of aminoguanidine. This assay method is mostly for the inhibitors of late glycation and AGE formation (post-Amadori). The results obtained by this assay show all ten compounds investigated here have strong inhibitory effects on post-Amadori glycation, AGE formation and AGE crosslinking.

TABLE 2

Percent Inhibition by LR93–LR102 in the BSA-Glucose Assay

| Compound | Percent Inhibition |
| --- | --- |
| AG | 74.0 |
| LR93 | 35 |
| LR94 | 26.8 |
| LR95 | 34 |
| LR96 | 30 |
| LR97 | 26.2 |
| LR98 | 26.7 |
| LR99 | 30.9 |
| LR100 | 31.9 |
| LR101 | 32.1 |
| LR102 | 53 |

EXAMPLE 3

N-Acetyl-Glycyl-Lysine Methyl Ester (G.K. Peptide)-Ribose Assay

Evaluation of the late glycation products (AGEs), and AGE-inhibition by the new inhibitor compounds was tested by incubation of G.K. peptide in ribose in the presence or the absence of the agent, followed by determination of chromophores generated in the course of glycation and AGE formation through determination of their specific fluorescence. The Nagaraj et al. (1996) method used to evaluate the ability of the compounds of the present invention to inhibit the crosslinking of N-acetylglycyl-lysine methyl ester in the presence of ribose was as follows:

Stock Solutions:

0.5 M sodium phosphate buffer pH 7.4 containing $NaN_3$ 0.2 g/L

GK peptide (Sigma) 80 mg/mL in 0.5 M sodium phosphate buffer pH 7.4

Ribose 800 mM (120 mg/mL) in 0.5 M phosphate buffer

Triplicate samples of equal volumes (0.1 mL) of the 3 stock solutions were mixed together, filtered through a 0.2 micron filter (Corning) and incubated under aseptic conditions for 24 hours at 37° C. The inhibitor compounds were added to a final concentration of 1 millimole/L. At the end of the incubation period, samples were analyzed for their specific fluorescence (excitation, 330 nm; emission, 415 nm). The % inhibition by different concentrations of inhibitor was calculated as described above. Aminoguanidine was used at 50 mM as a positive control.

Figure 3:
FIG. 3 shows the inhibition by LR93–LR102 in the G.K. Peptide-Ribose Assay. The bars are the same as for FIG. 2.

FIG. 3 shows the inhibitory effects of the compounds to block specific fluorescence of protein-AGE in these separate determinations, using G.K. peptide-ribose assay. Results are shown in Table 3. The results of this assay indicate that all ten compounds investigated here have strong inhibitory effects and block specific fluorescence of proteins AGE in these separate determinations.

TABLE 3

Percent Inhibition by LR93–LR102 in the G.K.-Ribose Assay

| Compound | Percent Inhibition |
|---|---|
| AG | 67 |
| LR93 | 42.8 |
| LR94 | 33.7 |
| LR95 | 29.5 |
| LR96 | 42.4 |
| LR97 | 33.3 |
| LR98 | 37.3 |
| LR99 | 39.5 |
| LR100 | 28.5 |
| LR101 | 40.1 |
| LR102 | 35.1 |

EXAMPLE 4

ELISA Assay

A special ELISA technique (Al-abed et al., 1999) was used to evaluate the ability of the compounds being studied to inhibit the crosslinking of glycated-BSA (AGE-BSA) to a rat tail-tendon-collagen coated 96 well plate (Biocoat Cell Environment, Becton Dickinson). Crosslinking of AGE-BSA to a rat tail-tendon-collagen coated plate was performed with and without the testing compound at the desired concentrations. The uncross-linked AGE-BSA was then removed by washing the wells. The AGE-BSA crosslinked to the tail-tendon-collagen coated plate was then quantified by a polyclonal antibody raised against AGE-RNase in our laboratory. Positive results in the assay indicate that the inhibitor is capable of reducing the amount of AGE-BSA which crosslinks with collagen. Aminoguanidine was used as positive control.

Figure 4A:
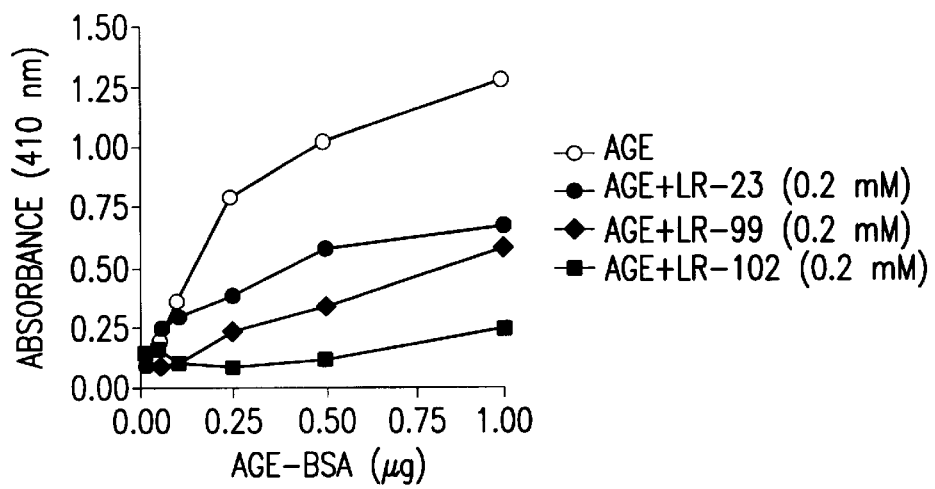
FIGS. 4A–C show the results for compounds LR23, LR96, LR99 and LR102 in the ELISA assay.
Figure 4B:
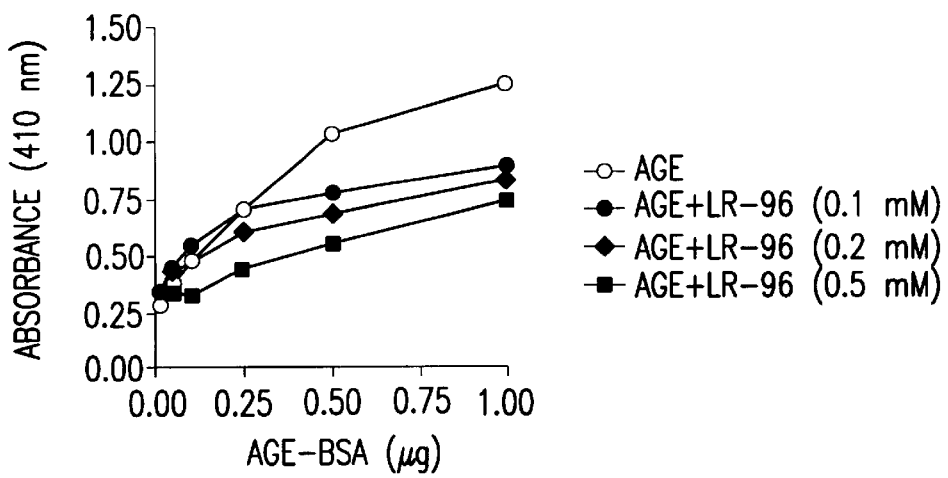
Figure 4C:
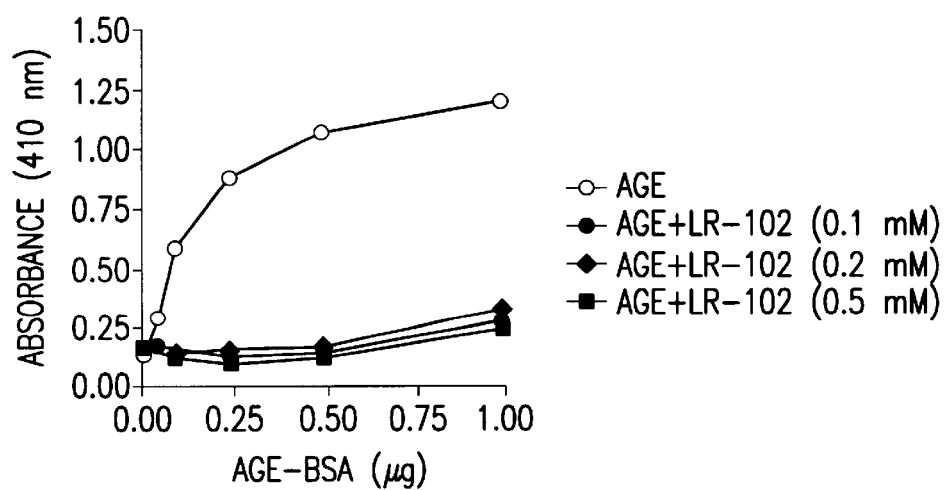
Figure 5:
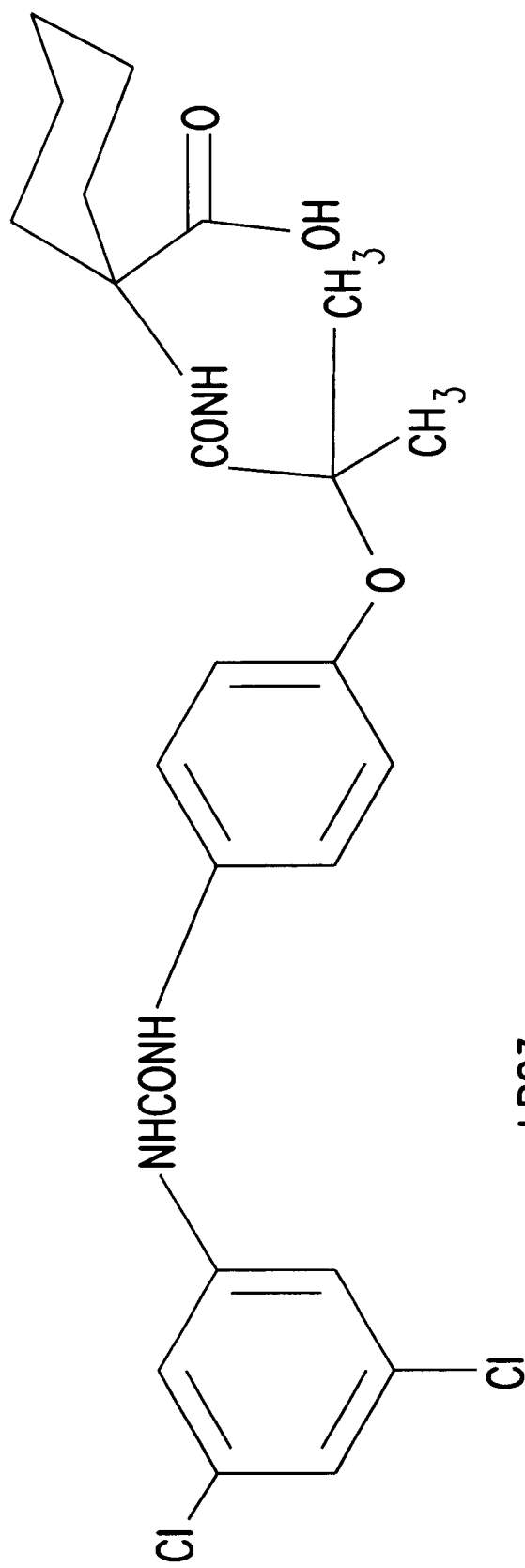
FIG. 5 shows the structure of compound LR23.
Figure 6:
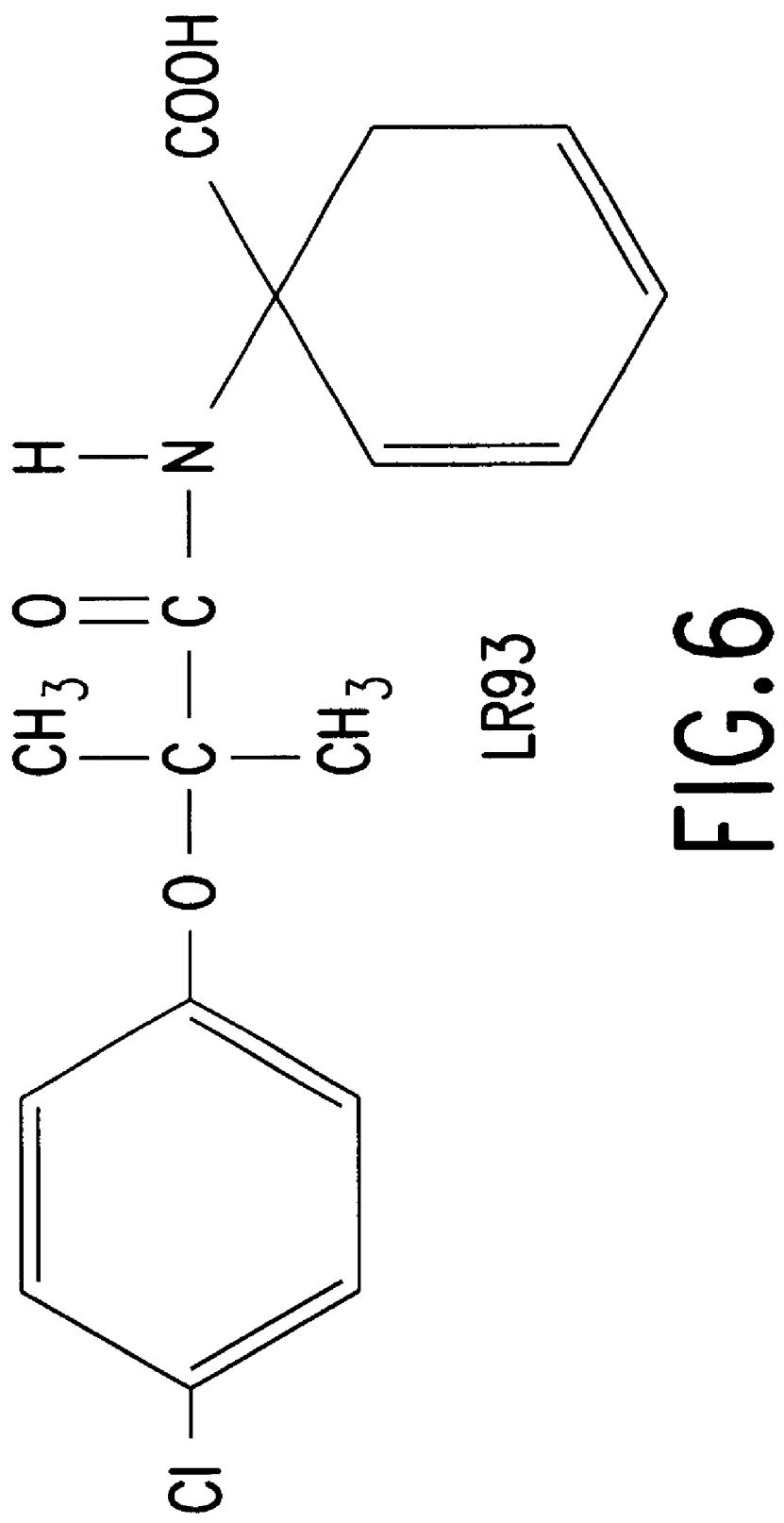
FIG. 6 shows the structure of compound LR93.
Figure 7:
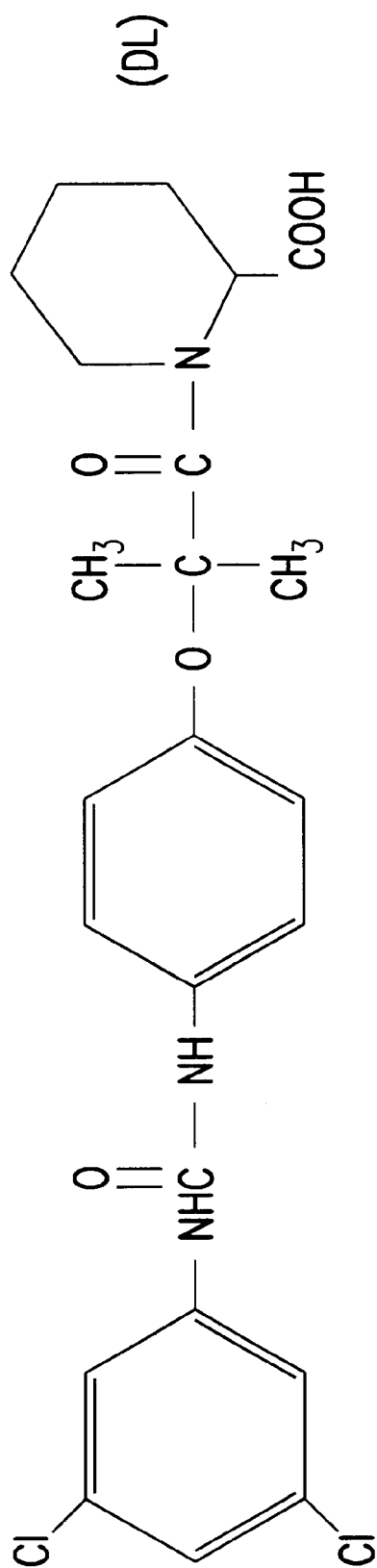
FIG. 7 shows the structure of compound LR94.
Figure 8:
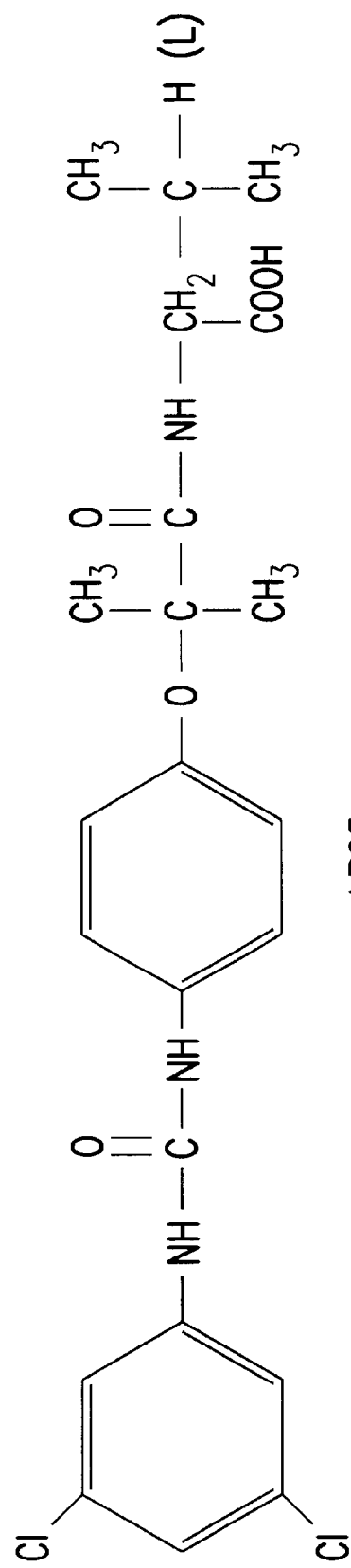
FIG. 8 shows the structure of compound LR95.
Figure 9:
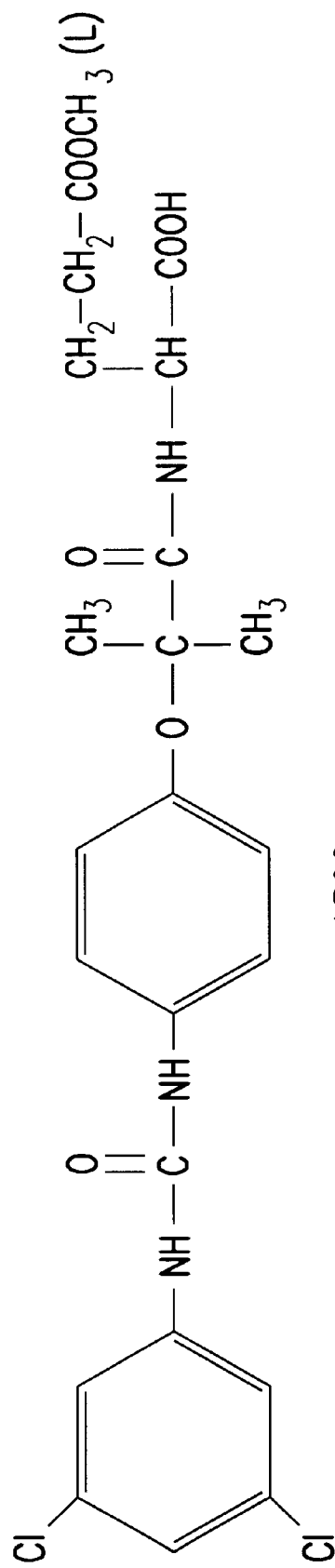
FIG. 9 shows the structure of compound LR96.
Figure 10:
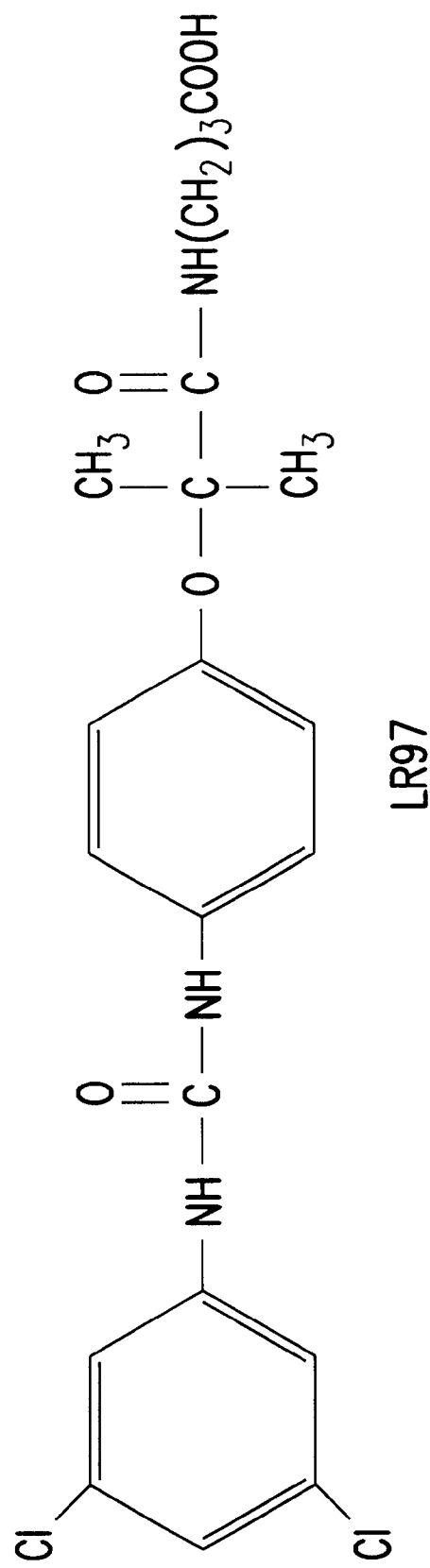
FIG. 10 shows the structure of compound LR97.
Figure 11:
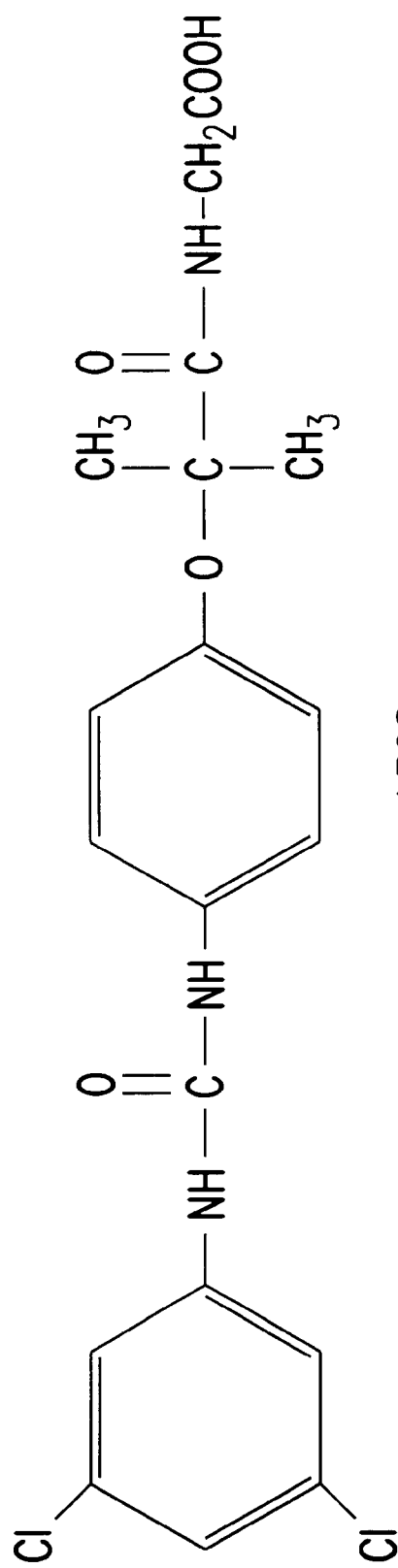
FIG. 11 shows the structure of compound LR98.
Figure 12:
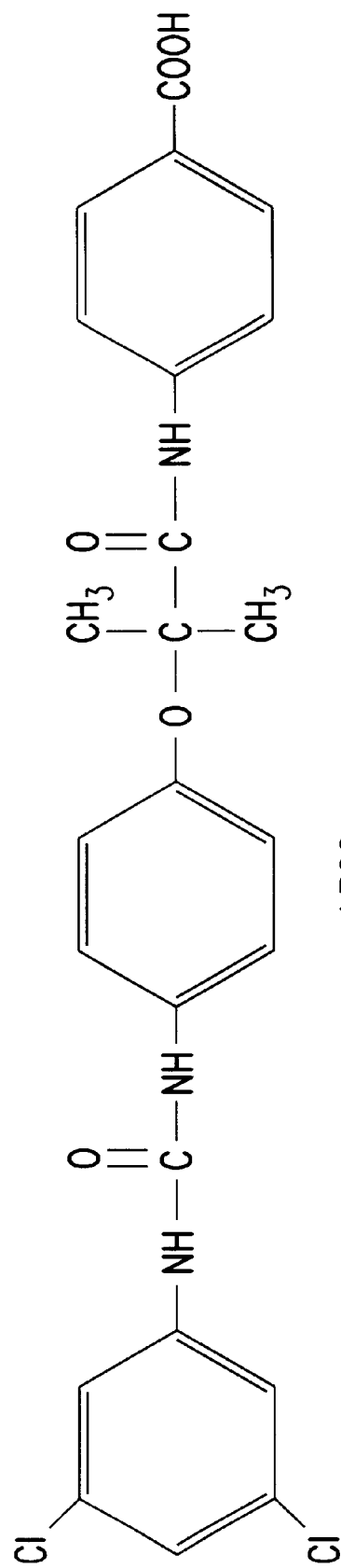
FIG. 12 shows the structure of compound LR99.
Figure 13:
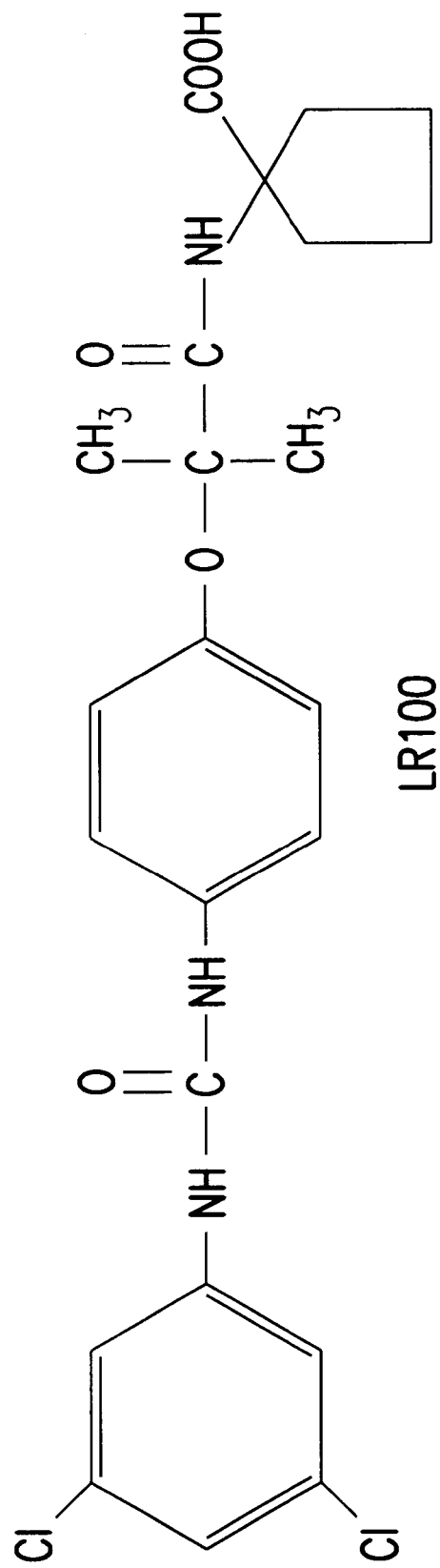
FIG. 13 shows the structure of compound LR100.
Figure 14:
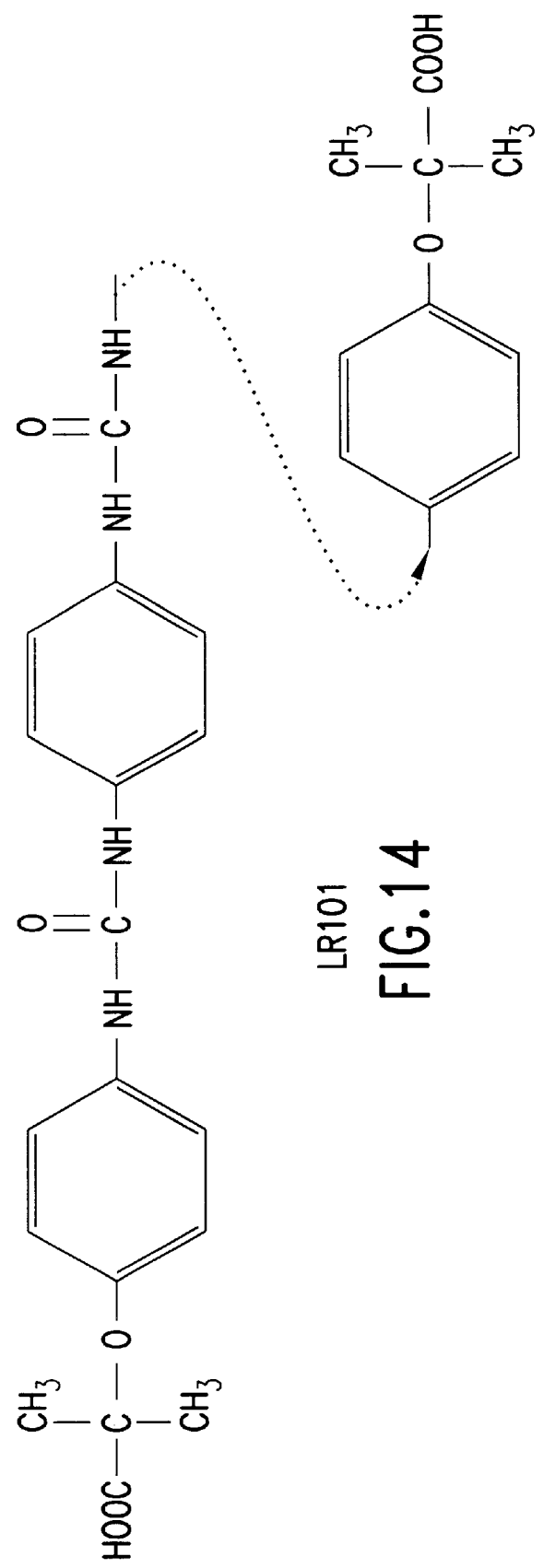
FIG. 14 shows the structure of compound LR101.
Figure 15:
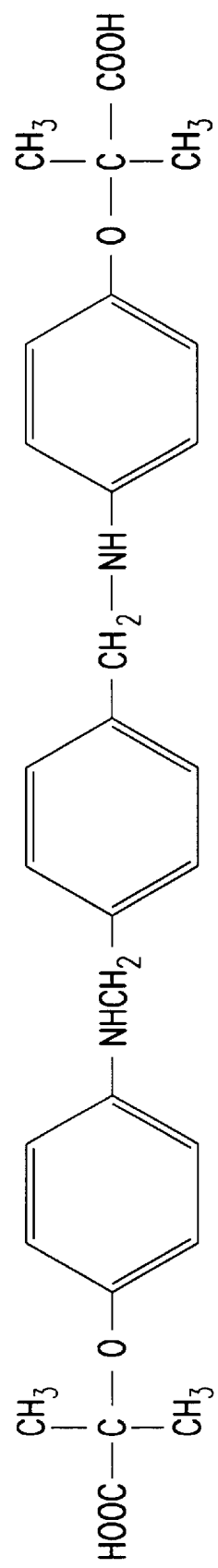
FIG. 15 shows the structure of compound LR102.

The results using compounds LR96, LR99 and LR102 are shown in FIGS. 4A–C. These compounds are among a number of strong inhibitors of AGE-protein crosslinking.

The above Examples indicate that this type of drug therapy will be beneficial in reducing the pathology associated with the formation of nonenzymatic glycation products (early and late products) and protein—protein crosslinking. Compounds of the present invention are found to be up to 250 times more potent inhibitors of AGE-fornation in vitro as compared to aminoguanidine which is in phase 2/3 clinical trial to prevent diabetic complications. These compounds can be administered orally at variable dosages depending on the activity of each agent in a single or individual amounts. In addition, the compounds can be administered parenterally or rectally.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Airaksinen K E J, et al. (1993). *Cardiovas. Res.* 27:942–945.
Al-Abed Y, et al. *J. Biol. Chem.* 271:2892–2896.
Al-Abed Y, et al. (1999). *Methods in Enzymology* 309:152–172.
Bailey A J, et al. (1998). *Mech. Ageing Dev.* 106:1–56.
Baynes J W and Thorpe S R (1999). *Diabetes* 48:1–9.
Beisswenger P, et al. (1998). *Am. Diab. Assoc.,* 58th Annual Meeting, #312, Chicago.
Boel E, et al. (1995). *J. Diab. Compl.* 9:104–129.
Booth A A, et al. (1997). *J. Biol. Chem.* 272:5430–5437.
Brownlee M, et al. (1985). *Diabetes* 34:938–941.
Brownlee M, et al. (1986). *Science* 232:1629–1632.
Brownlee M, et al. (1991). *N. Engl. J. Med.* 318:1315–1321.
Bucala R and Cerami A (1992). *Adv. Pharmacol.* 23:1–33.
Bucala R and Rahbar S (1998). *Protein Glycation and Vascular Disease in Endocrinology of Cardiovascular Function.* Edited by E. R. Levin and J. L. Nadler, Kluwer Acad. Publishers, pp. 159–180.
Bucala R and Viassara H (1997). *Experimental Physiology* 82:327–337.
Bucala R, et al. (1984). *Proc. Natl. Acad. Sci. USA* 81:105–109.
Bucala R, et al. (1993). *Proc. Natl. Acad. Sci. USA* 90:6434–6438.
Bucala R, et al. (1994). *Proc. Natl. Acad. Sci. USA* 91:9441–9445.
Cameron N E, et al. (1992). *Diabetologia* 35:946–950.
Corbett J A, et al. (1992). *Diabetes* 41:552–556.
Dawnay A and Millar D J (1998). *Cell. Mol. Biol. (Noisy-le-grand)* 44:1081–1094.
Diabetes Control and Complications Trial Research Group (1993). *N. Engl. J. Med.* 329:977–986.
Durany N, et al. (1999). *Eur. Arch. Psychiatry Clin. Neurosci.* 249 Suppl. 3:68–73.
Edelstein D and Brownlee M (1992). *Diabetes* 41:26–29.
Haitoglou C S, et al. (1992). *J. Biol. Chem.* 267:12404–12407.
Hammes H, et al. (1991). *Proc. Natl. Acad. Sci. USA* 88:11555–11563.
Harding J J (1990). *Arch. Opthalmol.* 108:13–14.
He C, et al. (1999). *Diabetes* 48:1308–1315.
Hedrick C C, et al. (2000). *Diabetologia* 43:312–320.
Hirsch J, et al. (1992). *Carbohydrate Res.* 232:125–130.
Horie K, et al. (1997). *J. Clin. Invest.* 100:2995–3004.
Iijima K, et al. (2000). *Biochem. J.* 347:23–27.
Ikeda K, et al. (1996). *Biochemistry* 35:8075–8083.

Itakura M, et al. (1991). *Life Science* 49:889–897.
Kato H, et al. (1990). *Biochim. Biophys. Acta* 1035:71–76.
Kato S, et al. (1999). *Acta Neuropathol. (Berl.)* 97:260–266.
Kato S, et al. (2000). *Acta Neuropathol.* 100:490–505.
Kennedy L and Lyons T J (1997). *Metabolism* 46:14–21.
Khalifah R G, et al. (1996). *Biochemistry* 35:4645–4654.
Khalifah R G, et al. (1999). *Biochem. Biophys. Res. Commun.* 257:251–258.
Kikuchi S, et al. (1999). *J. Neurosci. Res.* 57:280–289.
Kochakian M, et al. (1996). *Diabetes* 45:1694–1700.
Koschinsky T, et al. (1997). *Proc. Natl. Acad. Sci. USA* 94:6474–6479.
Lalezari I, et al. (1988). *Proc. Natl. Acad. Sci. USA* 85:6117–6121.
Lalezari I and Lalezari P (1989). *J. Med. Chem.* 32:2352–2357.
Lapolla A, et al. (2000). *J. Am. Soc. Mass. Spectrom.* 11: 153–159.
Li Y M, et al. (1996). *Proc. Natl. Acad. Sci. US.A.* 93:3902–3907.
Lindsay M R, et al. (1997). *Clin. Chem. Acta* 263:239–247.
Lucey M D, et al. (2000). *J. Rheumatol.* 27:319–323.
Maillard L C(1916). *Ann. Chem.* 5:258.
Makita Z, et al. (1991). *N. Eng. J. Med.* 325:836–842.
Makita Z, et al. (1992). *Science* 258:651–653.
Makita Z, et al. (1994). *Lancet* 343:1519–1522.
Matsumoto K, et al. (1997). *Biochem. Biophys. Res. Commun.* 241:352–354.
McLellan A C, et al. (1994). *Clin. Sci.* 87:21–29.
McPherson J D, et al. (1988). *Biochemistry* 27:1901–1907.
Miyata T, et al. (1993). *J. Clin. Invest.* 92:1243–1252.
Monnier V, et al. (1986). *N. Engl. J. Med.* 314:403–408.
Munch G, et al. (1997). *Brain Res. Brain Res. Rev.* 23:134–143.
Munch G, et al. (1998). *J. Neural. Transm.* 105:439–461.
Nagai R, et al. (2000). *Diabetes* 49:1714–1723.
Nagaraj R H, et al. (1996).*J. Biol. Chem.* 271:19338–19345.
Nakamura S, et al. (1997). *Diabetes* 46:895–899.
Newkirk M M, et al. (1998). *Cell. Mol. Biol. (Noisy-le-grand)* 44:1129–1138.
Nicholl I D and Bucala R (1998). *Cell. Mol. Biol. (Noisy-le-grand)* 44:1025–1033.
Nicholls K and Mandel T (1989). *Lab. Invest.* 60:486–491.
Odani H, et al. (1999).*J. Chromatogr. B Biomed. Sci. Appl.* 731:131–140.
O'Harte F P M, et al. (2000). *Peptides* 21:1519–1526.
Onorato J M, et al. (1998). *Ann. N.Y. Acad. Sci.* 854:277–290.
Panagiotopoulos S, et al. (1998). *Atherosclerosis* 136:125–131.
Park L, et al. (1998). *Nat. Med.* 4:1025–1031.
Phillips S A and Thornalley P J (1993). *Eur. J. Biochem.* 212:101–105.
Rahbar S (1968). *Clin. Chem. Acta* 22:296–298.
Rahbar S, et al. (1969). *Biochem. Biophys. Res. Commun.* 36:838–843.
Rahbar S, et al. (1987). *Blood* 70 (Suppl. 1):171.
Rahbar S, et al. (1999). *Biochem. Biophys. Res. Commun.* 262:651–656.
Rahbar S, et al. (2000). *Mol. Cell. Biol. Res. Comm.* 3:360–366.
Rahbar S and Nadler J L (1999). *Clin. Chim. Acta* 287:123–130.
Requena J R, et al. (1993). *Diabetes Res. Clin. Pract.* 19:23–30.
Requena J R, et al. (1997).*J. Biol. Chem.* 272:17473–17479.
Ruggiero-Lopez D, et al. (1999). *Biochem. Pharmacol.* 58:1765–1773.
Sano H, et al. (1999). *Mech. Ageing Dev.* 107:333–346.
Schalkwijk C G, et al. (1998). *Biochim. Biophys. Acta* 1394:187–198.
Schmidt A M, etal. (1994). *Proc. Natl. Acad. Sci. USA* 91:8807–8811.
Sensi M, et al. (1993). *Diabetologia* 36:797–801.
Shibata N, et al. (1999). *Acta Neuropathol. (Berl.)* 97:240–246.
Silbiger S, et al., (1993). *Kidney Int.* 43:853–864.
Slatter D A, et al. (2000). *Diabetologia* 43:550–557.
Soulis T, et al. (1997). *Diabetologia* 40:1141–1151.
Soulis-Liparota T, et al. (991). *Diabetes* 40:1328–1334.
Takagi Y, et al. (1995). *J. Diabetes Compl.* 9:87–91.
Takahashi M, et al. (1997). *J. Biol. Chem.* 272:3437–3443.
Takayama F, et al. (1998). *Cell. Mol. Biol. (Noisy-le-grand)* 44:1101–1109.
Taneda S and Monnier V M (1994). *Clin. Chem.* 40:1766–1773.
Tilton R G, et al. (1993). *Diabetes* 42:221–232.
Ulrich P and Zhang X (1997). *Diabetologia* 40:5157–5159.
Vasan S, et al. (1996). *Nature* 382:275–278.
Verbeke P, et al. (2000). *Biochim. Biophys. Acta* 1502:481–494.
Vlassara H (1994). *J. Lab. Clin. Med.* 124:19–30.
Vlassara H, et al. (1994). *Lab. Invest.* 70: 138–151.
Vlassara H, et al. (1995). *Mol. Med.* 1:447–456.
Westwood M E, et al. (1997). *Biochim. Biophys. Acta* 1356:84–94.
Yan H and Harding J J (1999). *Biochim. Biophys. Acta* 1454:183–190.
Yan S D, et al. (1997). *Eur. J. Clin. Invest.* 27:179–181.
Yim H S, et al. (1995). *J. Biol. Chem.* 270:28228–28233.

Patents

U.S. Pat. No. 4,921,997
U.S. Pat. No. 5,093,367
U.S. Pat. No. 5,268,500
U.S. Pat. No. 5,292,935
U.S. Pat. No. 5,661,139

What is claimed is:

1. A method of inhibiting formation of glycation endproducts or protein crosslinking in an organism, wherein said method comprises administering an effective amount of a compound or a pharmaceutically acceptable salt of said compound to said organism wherein said compound is selected from the group consisting of:

LR93: 1-[4-chlorophenoxyisobutyrylamido]1-cyclohexane carboxylic acid,

LR94: DL-4-(3,5-dichlorophenylureidophenoxyisobutyrylpiperdine)-2-carboxylic acid, LR95: L-4-(3,5-dichlorophenylureidophenoxyisobutyryl) leucine, LR96: L-4-(3,5-diclorophenylureidophenoxyisobutyryl) glutamic acid gamma methyl ester, LR97: gamma-4-(3,5-dichlorophenylureidophenoxyisobutyrylamido) butyric acid, LR98: 4-(3,5-dichlorophenylureidophenoxyisobutyrylamido) acetic acid, LR99: 4-(3,5-dichlorophenylureidophenoxyisobutyryl)-4 amino benzoic acid, LR100: 1,4-(3,5-dichlorophenylureidophenoxyisobutyrylamido)-1-cyclopentane carboxylic acid, LR101: 1,4-benzene-bis-(ureidophenoxyisobutyric acid), and LR102: 1,4-benzene-bis-(4-methyleneamino- phenoxyisobutyric acid).

2. A method of slowing deleterious effects of aging in an organism wherein said effects are formation of glycation endproducts or protein crosslinking, wherein said method comprises administering an effective amount of a compound or a pharmaceutically acceptable salt of said compound to said organism wherein said compound is selected from the group consisting of:

LR93: 1-[4-chlorophenoxyisobutyrylamido]1-cyclohexane carboxylic acid,

LR94: DL-4-(3,5-dichlorophenylureidophenoxy-isobutyrylpiperdine)-2-carboxylic acid, LR95: L-4-(3,5-dichlorophenylureidophenoxyisobutyryl) leucine, LR96: L-4-(3,5-diclorophenylureidophenoxyisobutyiyl) glutamic acid gamma methyl ester, LR97: gamma-4-(3,5-dichlorophenylureidophenoxy-isobutyrylamido) butyric acid, LR98: 4-(3,5-dichlorophenylureidophenoxy-isobutyrylamido) acetic acid, LR99: 4-(3,5-dichlorophenylureidophenoxyisobutyryl)-4 amino benzoic acid, LR100: 1,4-(3,5-dichlorophenylureidophenoxy-isobutyrylamido)-1-cyclopentane carboxylic acid, LR101: 1,4-benzene-bis-(ureidophenoxyisobutyric acid), and LR102: 1,4-benzene-bis-(4-methyleneaminophenoxy-isobutyric acid).

3. A method of slowing progress in a patient of complications resulting from diabetes wherein said complications result from formation of glycation endproducts or protein crosslinking, wherein said method comprises administering an effective amount of a compound or a pharmaceutically acceptable salt of said compound to said patient wherein said compound is selected from the group consisting of:

LR93: 1-[4-chlorophenoxyisobutyrylamido]1-cyclohexane carboxylic acid,

LR94: DL-4-(3,5-dichlorophenylureidophenoxy-isobutyrylpiperdine)-2-carboxylic acid, LR95: L-4-(3,5-dichlorophenylureidophenoxyisobutyryl) leucine, LR96: L-4-(3,5-diclorophenylureidophenoxyisobutyryl) glutamic acid gamma methyl ester, LR97: gamma-4-(3,5-dichlorophenylureidophenoxy-isobutyrylamido) butyric acid, LR98: 4-(3,5-dichlorophenylureidophenoxy-isobutyrylamido) acetic acid, LR99: 4-(3,5-dichlorophenylureidophenoxyisobutyryl)-4 amino benzoic acid, LR100: 1,4-(3,5-dichlorophenylureidophenoxy-isobutyrylamido)-1-cyclopentane carboxylic acid, LR101: 1,4-benzene-bis-(ureidophenoxyisobutyric acid), and LR102: 1,4-benzene-bis-(4-methyleneaminophenoxy-isobutyric acid).

4. A method of slowing progress in a patient of rheumatoid arthritis, Alzheimer's disease, uremia, neurotoxicity, or atherosclerosis, wherein said method comprises administering an effective amount of a compound or a pharmaceutically acceptable salt of said compound to said patient wherein said compound is selected from the group consisting of:

LR93: 1-[4-chlorophenoxyisobutyrylamido]1-cyclohexane carboxylic acid,

LR94: DL-4-(3,5-dichlorophenylureidophenoxy-isobutyrylpiperdine)-2-carboxylic acid, LR95: L-4-(3,5-dichlorophenylureidophenoxyisobutyryl) leucine, LR96: L-4-(3,5-diclorophenylureidophenoxyisobutyryl) glutamic acid gamma methyl ester, LR97: gamma-4-(3,5-dichlorophenylureidophenoxy-isobutyrylamido) butyric acid, LR98: 4-(3,5-dichlorophenylureidophenoxy-isobutyrylamido) acetic acid, LR99: 4-(3,5-dichlorophenylureidophenoxyisobutyryl)-4 amino benzoic acid, LR100: 1,4-(3,5-dichlorophenylureidophenoxy-isobutyrylamido)-1-cyclopentane carboxylic acid, LR101: 1,4-benzene-bis-(ureidophenoxyisobutyric acid), and LR102: 1,4-benzene-bis-(4-methyleneaminophenoxy-isobutyric acid).

5. A method of preventing spoilage of proteins in foodstuffs wherein said method comprises mixing an effective amount of a compound or a pharmaceutically acceptable salt of said compound with said foodstuffs, wherein said effective amount inhibits formation of glycation endproducts or protein crosslinking, wherein said compound is selected from the group consisting of:

LR93: 1-[4-chiorophenoxyisobutyrylamido]1-cyclohexane carboxylic acid,

LR94: DL-4-(3,5-dichlorophenylureidophenoxy-isobutyrylpiperdine)-2-carboxylic acid, LR95: L-4-(3,5-dichlorophenylureidophenoxyisobutyryl) leucine, LR96: L-4-(3,5-diclorophenylureidophenoxyisobutyryl) glutamic acid gamma methyl ester, LR97: gamma-4-(3,5-dichlorophenylureidophenoxy-isobutyrylamido) butyric acid, LR98: 4-(3,5-dichlorophenylureidophenoxy-isobutyrylamido) acetic acid, LR99: 4-(3,5-dichlorophenylureidophenoxyisobutyryl)-4 amino benzoic acid, LR100: 1,4-(3,5-dichlorophenylureidophenoxy-isobutyrylamido)-1-cyclopentane carboxylic acid, LR101: 1,4-benzene-bis-(ureidophenoxyisobutyric acid), and LR102: 1,4-benzene-bis-(4-methyleneaminophenoxyisobutyric acid).

6. A compound or a pharmaceutically acceptable salt of said compound wherein said compound is selected from the group consisting of:

LR93: 1-[4-chlorophenoxyisobutyrylamido]1-cyclohexane carboxylic acid,

LR94: DL-4-(3,5-dichlorophenylureidophenoxy-isobutyrylpiperdine)-2-carboxylic acid, LR95: L-4-(3,5-dichlorophenylureidophenoxyisobutyryl) leucine, LR96: L-4-(3,5-diclorophenylureidophenoxyisobutyryl) glutamic acid gamma methyl ester, LR97: gamma-4-(3,5-dichlorophenylureidophenoxy-isobutyrylamido) butyric acid, LR98: 4-(3,5-dichlorophenylureidophenoxy-isobutyrylamido) acetic acid, LR99: 4-(3,5-dichlorophenylureidophenoxy-isobutyryl)-4 amino benzoic acid, LR100: 1,4-(3,5-dichlorophenylureidophenoxy-isobutyrylamido)-1-cyclopentane carboxylic acid, LR101: 1,4-benzene-bis-(ureidophenoxyisobutyric acid), and LR102: 1,4-benzene-bis-(4-methyleneaminophenoxy-isobutyric acid).

7. A pharmaceutical composition comprising an effective amount of i) a compound or a pharmaceutically acceptable salt of said compound and ii) a pharmaceutical carrier, wherein said compound is a compound of claim 6.

* * * * *

UNITED STATES PATENT AND TRADEMARK OFFICE
CERTIFICATE OF CORRECTION

PATENT NO.   : 6,605,642 B2
DATED        : August 12, 2003
INVENTOR(S)  : Samuel Rahbar It is certified that error appears in the above-identified patent and that said Letters Patent is hereby corrected as shown below:

<u>Title page, Item [54] and Column 1, line 1</u>,
Title, insert -- NOVEL -- before the word "INHIBITORS".

<u>Column 3</u>,
Line 48, replace "Thomalley" with -- Thornalley --.

<u>Column 12</u>,
Line 6, replace "fornation" with -- formation --.

<u>Column 15</u>,
Line 15, replace "diclorophenylureidophenoxyisobutyiyl" with
-- diclorophenylureidophenoxyisobutyryl --.

<u>Column 16</u>,
Line 29, replace "chiorophenoxyisobutyrylamido" with
-- chlorophenoxyisobutyrylamido --.

Signed and Sealed this

Thirteenth Day of July, 2004

JON W. DUDAS
*Acting Director of the United States Patent and Trademark Office*